United States Patent [19]

Hässig et al.

[11] Patent Number: 4,721,616

[45] Date of Patent: Jan. 26, 1988

[54] TREATMENT OF VERNAL CONJUNCTIVITIS

[75] Inventors: Alfred Hässig, Stettlen; Urs E. Nydegger, Herrenschwanden, both of Switzerland

[73] Assignee: Swiss Red Cross, Bern, Switzerland

[21] Appl. No.: 20,048

[22] Filed: Feb. 27, 1987

Related U.S. Application Data

[63] Continuation of Ser. No. 689,396, Jan. 7, 1985, abandoned.

[30] Foreign Application Priority Data

Mar. 13, 1984 [GB] United Kingdom ................. 8406560

[51] Int. Cl.⁴ .......................................... A61K 39/395
[52] U.S. Cl. ....................................... 424/85; 424/101
[58] Field of Search ............................ 424/85, 101, 91

[56] References Cited

U.S. PATENT DOCUMENTS 3,903,262 9/1975 Pappenhagen et al. ............... 424/85
4,168,303 9/1979 Nishida et al. .......................... 424/85

FOREIGN PATENT DOCUMENTS 1422760 1/1976 United Kingdom .

OTHER PUBLICATIONS

Abernathy, Rosalind S., et al. Pediatrics, pp. 980–993, (Jun. 1958).
Thomas, Orville C., et al. Southern Medical Journal, vol. 57, pp. 498–504 (May, 1964).
Hilman, Bettina C., et al. JAMA, vol. 207, No. 5, pp. 902–906 (Feb. 1969).
Redner, Bernard, et al., JAMA, vol. 185, No. 9, pp. 692–695 (Aug. 1963).
Chem. Abs. vol. 93, Abstract No. 210233z, 1980.
J. Ring et al in Münch. Med. Wochenschrift 1983, 125, 289–92.
Clinical Opthamology vol. 4 (1978) by M. Allansmith.
Chapter 7, "Ocular Diseases with Immunologie Features" in Allergy and Immunology of the Eye (1979) by M. Friedlaender.

*Primary Examiner*—Blondel Hazel
*Attorney, Agent, or Firm*—Gerald D. Sharkin; Robert S. Honor; Thomas O. McGovern

[57] ABSTRACT

Vernal conjunctivitis is treated by administration of an intravenously injectable form of a polyvalent, intact immunoglobulin (IgG).

6 Claims, No Drawings

TREATMENT OF VERNAL CONJUNCTIVITIS

This is a continuation of application Ser. No. 689,396, filed Jan. 7, 1985, now abandoned.

This invention relates to the treatment of allergic disorders.

A particular form of allergic disorder is the eye disease known as vernal conjunctivitis. This disease affects mostly children and adolescents and occurs predominantly in the warm months of the year. It is characterised by keratinisation of the epithelium, with possible abrasion of the underlying cornea. It is believed to be caused by allergic response to air-borne allergens such as pollen.

It is known to use intramuscular injections of gamma globulin (IgG) in the treatment of allergic disorders, particularly respiratory allergy in children. However, such treatment has, in comparative studies, been found to be ineffective (i.e. the results obtained were not significantly better than those found for placebo). Intramuscular IgG does not appear to have been used in the treatment of vernal conjunctivitis.

Surprisingly, it has now been found that vernal conjunctivitis may be effectively treated by intravenous administration of a suitable immunoglobulin.

Accordingly, the present invention provides a method of treatment of vernal conjunctivitis, which method comprises administering an effective amount of an intravenously injectable form of a polyvalent, intact immunoglobulin (IgG).

The treatment may be either therapeutic or prophylactic in nature, that is, it may ameliorate an acute attack of vernal conjunctivitis or it may prevent the onset of acute attacks in chronically suscepible patients.

By a polyvalent, intact Ig is meant one which has not been cleaved (for example with high pepsin concentrations) and which retains the structural and functional integrity of the 7S-IgG antibodies. Preferably it is one obtained from blood serum fractions by a modified alcohol cryoprecipitation including mild acidification at pH 4. A suitable product is Immunoglobulin SRC produced by the Swiss Red Cross and sold by Sandoz Ltd. under the name Sandoglobulin ®. The in vitro characteristics of this material have been published by J. Romer et al. "Characterization of Various Immunoglobulin Preparations for intravenous Application. I. Protein Composition and Antibody Content and Characterization of Various Immunoglobulin Preparations for Intravenous Application. II. Complement Activation and Binding to Staphylococcus Protein A. "(Vox Sanguinis Vol. 42, No. 2 (pp. 62–73 and 74–80), 1982.

The Ig is preferably administered by intravenous infusion in the form of a 2–6% solution, more preferably as a 3% solution in sterile physiological saline. A suitable rate of infusion of a 3% solution is, for example, 10 to 20 drops/minute for the first 15 minutes, 20 to 30 drops/minute for a further 15 minutes and 40 to 50 drops/minute thereafter.

For optimum effect, Ig is preferably administered in from two to five separate infusions within one week, preferably upon successive days. The total dosage given in one course of treatment is preferably from 0.05 to 2 g/kg of body weight, more preferably from 0.2 to 0.5 g/kg. The amount of Ig administered in a single infusion is preferably not more than approx. 10 g, more preferably not more than approx. 6 g.

The course of treatment may be repeated at intervals of 3 weeks or longer as required. For example a susceptible patient may be given one prophylactic course of treatment annually in the spring.

No adverse side-effects are observed as a result of the intravenous Ig treatment. The treatment is particularly efficacious with children below the age of 14.

The following Examples illustrate the invention:

EXAMPLE 1

An eight year old boy had suffered from vernal conjunctivitis since the age of four, with typical itching and ptosis of the eyelid. He had been treated for the previous two years with local steroids and chloramphericol, and subsequently, because of the danger of secondary glaucoma and opacity of the lens, he had received prophylactic treatment with Optichrom ® (sodium cromoglycate). In spite of this, large pupillary foci had appeared on both upper eyelids, complicated with erosive corneal lesions.

Administration of 3 g of Sandoglobulin ® by intravenous infusion followed by a further infusion of 6 g Sandoglobulin gave a practically complete remission of symptoms, and the conjunctivae appeared practically disease-free on examination six months later.

EXAMPLE 2

A nine year old girl had suffered from vernal conjunctivitis since the age of five, predominantly in the right eye. She had relapses each spring and summer, with extreme itching and typical infection of bulbar conjunctivitae of both eyes; purple colouration with slight ptosis, pannus of corneae on both eyes and abundant eosinophilia of conjunctival smears.

After receiving 3 g Sandoglobulin by intravenous infusion, the patient showed clearcut improvement.

We claim:

1. A method of treatment of vernal conjunctivitis, which method comprises administering an effective amount of an intravenously injectable form of a polyvalent, intact immunoglobulin (IgG).

2. A method according to claim 1 in which the polyvalent intact immunoglobulin is obtained from blood serum fractions by a modified alcohol cryoprecipitation including mild acidification at pH 4.

3. A method according to claim 1 in which the immunoglobulin is administered in from two to five separate intravenous infusions, the total dosage given in one course of treatment being from 0.5 to 2 g/kg of body weight.

4. A method according to claim 3 in which the amount of immunoglobulin administered in a single infusion is not more than approx. 6 g.

5. A method according to claim 3 in which the intravenous infusion is in the form of a 2–6% solution in sterile physiological saline.

6. A method according to claim 3 in which the intravenous infusion is a 3% solution.

* * * * *